US006832912B2

(12) United States Patent
Mao

(10) Patent No.: US 6,832,912 B2
(45) Date of Patent: Dec. 21, 2004

(54) METHOD OF REALIGNING TEETH UTILIZING CYCLICAL FORCES

(75) Inventor: Jeremy Jian Mao, Chicago, IL (US)

(73) Assignee: The Board of Trustees of the University of Illinois, Chicago, IL (US)

(*) Notice: Subject to any disclaimer, the term of this patent is extended or adjusted under 35 U.S.C. 154(b) by 0 days.

(21) Appl. No.: 10/714,319

(22) Filed: Nov. 14, 2003

(65) Prior Publication Data

US 2004/0101800 A1 May 27, 2004

Related U.S. Application Data

(62) Division of application No. 09/957,770, filed on Sep. 21, 2001, now Pat. No. 6,648,639.
(60) Provisional application No. 60/234,530, filed on Sep. 22, 2000.

(51) Int. Cl.[7] .................................................. A61C 7/00
(52) U.S. Cl. ........................................................ 433/24
(58) Field of Search .............................. 433/24, 18, 20, 433/7, 5

(56) References Cited

U.S. PATENT DOCUMENTS

| 4,244,688 A | | 1/1981 | Kurz | |
|---|---|---|---|---|
| 4,255,138 A | | 3/1981 | Frohn | |
| 4,382,780 A | * | 5/1983 | Kurz | 433/5 |
| 4,579,779 A | | 4/1986 | Lieb | |
| 4,665,920 A | | 5/1987 | Campbell | |
| 4,883,046 A | * | 11/1989 | Fontenot | 601/38 |

OTHER PUBLICATIONS

Proffit et al., (1993) *Mosby Year Book*: St. Louis. pp. 266–288.
Brunelle et al., (1996) J. Dent. Res. 75 (Spec. Iss): 706–713.
Reitan (1951) Acta Odont. Scand. Suppl., 6:1–240.
Storey et al., (1952) Aust. J. Dent., 56:11–18.
Rygh et al., (1982) In Berkivitz et al. (Eds) *The Periodontal Ligament in Health and Disease*, Pergamon Press, Oxford, England, pp. 269–290.
Jager et al., (1993) Histochemistery, 100:161–166.
Ashizawa et al., (1993) Arch Oral Biol., 43(6):473–484.
Gu et al., (1999 Angle Orthod. 69(6):515–522.
Melsen (1999) Angle Orthod., 69(6):515–158.
Terai et al., (1999) J. Bone Miner. Res., 14(6):839–849.
Tsay et al., (1999) Am. J. Orthod. Dentofacial Orthop., 115(3):323–330.
Verna (1999) Bone, 24(4):671–379.
Van Leeuwen et al., (1999) Eur. J. Oral Sci., 107(6):468–474.
International Search Report for PCT/US01/29453 dated Nov. 12, 2003.

* cited by examiner

*Primary Examiner*—Kevin Shaver
*Assistant Examiner*—Melba Bumgarner
(74) *Attorney, Agent, or Firm*—Welsh & Katz, Ltd.

(57) ABSTRACT

Methods of treating malocclusion and inducing osteogenesis as well as an apparatus for treating malocclusion are described. The methods and apparatus utilize cyclic forces as compared to static forces to achieve their results.

7 Claims, 2 Drawing Sheets

METHOD OF REALIGNING TEETH UTILIZING CYCLICAL FORCES

CROSS-REFERENCE TO RELATED APPLICATION

This is a division of application Ser. No. 09/957,770, filed Sep. 21, 2001, now U.S. Pat. No. 6,648,639, whose disclosures are incorporated herein by reference and claim benefit of 60/234,530 filed Sep. 22, 2002.

BACKGROUND OF THE INVENTION

Orthodontics involves purposefully moving teeth towards a certain predefined pattern so that the tooth row has an esthetically pleasing look. The condition of crowded or crooked teeth is called malocclusion. Although ancient attempts to correct malocclusion date back to 1000 BC, modern orthodontics began slightly more than a century ago [Proffit et al., (1993) *Mosby Year Book*: St. Louis. pp. 266–288].

In late 1800s, Edward Angle placed metal bands on the teeth and used continuous wires that fit into the slots of the bands. Elastics were used to apply forces with a result of aligning the teeth along the "track" of the wire. The forces applied by Angle were static and continuous, meaning that once the forces have been generated by elastics, the forces are continuously present unless and until they decayed to nil.

Since Angle's practice, orthodontists have used static forces to induce orthodontic tooth movement. Contemporary orthodontic treatment takes an average of two years to complete in one patient, involving multiple visits and repeated activations; i.e., reasserting the force on the teeth. No one has attempted to determine whether cyclic forces; i.e., forces with rapidly varying magnitude over time, induce more rapid tooth movement than the presently used continuous forces.

Orthodontics involves the use of mechanical forces to move teeth within the jaw bone and therefore, relies on force-induced bone remodeling. A force is a physical quantity and has several essential properties such as the magnitude, direction, point of application and frequency. All these properties of orthodontic forces have been subjects of scientific research and considered in clinical practice of orthodontics with the exception of force frequency. Exclusive use of continuously applied static forces in orthodontics and the resulting lack of consideration of force frequency contradict the overall scientific consensus-based evidence obtained from orthopedic studies of long bones that cyclic forces induce more effective bone remodeling than static forces of matching magnitude.

The main advantage of the current orthodontic technology of using continuously applied static forces to move the teeth towards predetermined positions to achieve esthetically pleasing look is its predictable, albeit slow, outcome, inducing controlled tooth movement towards predetermined position when treatment is carried out by a competent orthodontist. The principal shortcoming of the current technology is its requirement of excessively long treatment duration: approximately two years on average. The essential reason for this excessively long treatment duration is due to a lack of efficiency resulting from the present use of continuously applied static forces.

More specifically, except as described hereinafter, only continuously applied static forces have been studied and/or used in previous studies and clinical practice in orthodontics. First, about 36 percent of the US population receive orthodontic treatments [Brunelle et al., (1996) *J. Dent. Res.*, 75(Spec Iss):706–713]. Continuously applied static forces are used on a daily basis for orthodontic tooth movement in these patients. Second, in addition to day-to-day practice of application of continuously applied static forces in clinical orthodontics, orthodontic tooth movement has been simulated in animal models with elastics and coil springs [Reitan (1951) *Acta Odont. Scand. Suppl.*, 6:1–240; Storey et al., (1952) *Aust. J. Dent.*, 56:11–18; Pygh et al., (1982) In Berkivitz et al. (Eds) *The Periodontal Ligament in Health and Disease*, Pergamon Press, Oxford, England, pp. 269–290; Jager et al., (1993) *Histochemistry*, 100:161–166; Ashizawa et al., (1998) *Arch Oral Biol.*, 43(6):473–484; Gu et al., (1999 *Angle Orthod.* 69(6):515–522; Melsen (1999) *Angle Orthod.*, 69(2):151–158; Terai et al.,(1999) *J. Bone Miner. Res.*, 14(6): 839–849; Tsay et al., (1999) *Am. J. Orthod. Dentofacial Orthop.*, 115(3):323–330; and Verna (1999) *Bone*, 24(4):371–379]. Without exception, continuously applied static forces have been used in all these studies.

Although there have been previous attempts to use "intermittent forces", the nature of the intermittent forces were static forces applied intermittently over time, for instance, two hours on and two hours off [Reitan (1951) *Acta Odont. Scand. Suppl.*, 6:1–240; van Leeuwen et al., (1999) *Eur. J. Oral Sci.*, 107(6):468–474] instead of the hereinafter described cyclic forces that rapidly change magnitude over short time, e.g. several cycles per second. The current technology of continuous, constant and static forces, such as those used in orthodontics, lacks either frequency modulation or change in force magnitude over time.

In addition to a lack of consideration of force frequency in both research studies and clinical practice of orthodontics as described above, both the threshold force and the duration of force application, which are two additional essential properties of a force, are not clearly understood in the field of orthodontics. First, a minimum of 6 hours has been thought to be the threshold below which orthodontic tooth movement does not occur [Proffit et al., (1993) *Mosby Year Book*: St. Louis. pp. 266–288]. However, this projected minimum threshold of 6 hours per day by Proffit et al. is largely theoretical, as stated in the caption of FIGS. 9–12 on page 275 of that work.

Although empirical clinical experience appears to support the notion that orthodontic forces must be applied beyond certain daily duration in order to induce tooth movement, the precise minimum daily duration is unclear. What appears of more significance than daily minimum duration is the overall duration of orthodontic treatment in association with current technology. The use of cyclic forces in orthodontic tooth movement described hereinafter can significantly shorten the present average two-year duration of orthodontic tooth movement.

Although there are more data on the threshold force magnitude required for tooth movement, the precise threshold is yet to be determined. In general a few hundred grams of force have been implicated to be the threshold for tooth movement. However, there remain projections as "theoretically, there is no doubt that light continuous forces produce the most efficient tooth movement" [Proffit et al., (1993) *Mosby Year Book*: St. Louis. pp. 266–288]. Although it has been shown that proliferation of periodontal ligament cells is greater in response to continuous forces than to intermittent forces of the same magnitude [Reitan (1951) *Acta Odont. Scand. Suppl.*, 6:1–240], the previously investigated intermittent forces were static forces applied intermittently over time [Reitan (1951) *Acta Odont. Scand.*

*Suppl.*, 6:1–240; van Leeuwen et al., (1999) *Eur. J. Oral Sci.*, 107(6):468–474] instead of the presently proposed cyclic forces that rapidly change magnitude within time units of seconds.

Contemporary orthodontists not only use braces to align the teeth, they also use orthopedic appliances such as headgear and facemask to change the shape of facial bones so that the overall facial shape is esthetically pleasant. The present technology (described hereinafter), in addition to providing a mechanism for rapidly aligning the teeth, also provides pathways by which the shape of facial bones can be rapidly changed, although the precise characteristics of the forces responsible for the two approaches are different. The present invention that is described hereinafter provides for the remodeling of craniofacial bones and treatment of malocclusion through the use of cyclic force application to the region to be remodeled.

BRIEF SUMMARY OF THE INVENTION

In accordance with the present invention, cyclic forces are used to expedite the remodeling of craniofacial bones to correct dentofacial deformities and expedite the remodeling of alveolar bone to treat malocclusion. One aspect of the invention contemplates a method for inducing a predetermined amount of osteogenesis in the craniofacial bones of a mammal in need thereof. That method comprises the steps of (a) applying cyclic forces to a craniofacial suture region of the mammal in which osteogenesis is desired with a peak magnitude of up to about 10 Newtons, and preferably about 0.1 to about 5 Newtons, and frequencies of up to about 40 Hz, and preferably about 0.1 to about 8 Hz, for a predetermined period of time. That application is (b) repeated a plurality of times until a predetermined amount of osteogenesis is obtained.

Another aspect of the invention contemplates a method for realigning one or more of the teeth of a mammal in need thereof. That method comprises the steps of (a) applying cyclic forces to at least one tooth of the mammal in which tooth realignment is desired with a peak magnitude of about 10 Newtons, and preferably about 0.1 to about 5 Newtons, and a frequency of up to about 40 Hz, and preferably about 0.1 to about 8 Hz, in a direction of the desired realignment for a predetermined period of time. That application is (b) repeated a plurality of times until a predetermined amount of tooth realignment is obtained.

A particular apparatus for treating malocclusion is another contemplated aspect of this invention. This apparatus comprises a band and bracket of generally inelastic material that are affixable to one or more teeth. The band has first and second ends that are joined at a centralized hub. A power source connected to an actuator assembly is provided to generate cyclic mechanical forces with a peak magnitude of up to about 10 Newtons, and preferably about 0.1 to about 5 Newtons, and a frequency of up to about 40 Hz, and preferably about 0.1 to about 8 Hz in a direction of the desired realignment desired at the centralized hub and thereby to the band. The power source and actuator are controlled by a microprocessor that can direct the duration of the application of the force as well as the repeated application of the cyclic mechanical force.

A method for treating malocclusion to realign teeth in a mammal in need thereof is another contemplated aspect of this invention. This method comprises the steps of providing a band of generally inelastic material that is affixed to one or more teeth of the mammal to be treated. The ends of the band are joined at a centralized hub. A power source connected to an actuator assembly is used to apply cyclic mechanical forces with a peak magnitude of up to about 10 Newtons, and preferably about 0.1 to about 5 Newtons, and a frequency of up to about 40 Hz, and preferably about 0.1 to about 8 Hz, in a direction of the desired realignment desired at the centralized hub and thereby to the band, the cyclic forces being applied for a predetermined time period. The power source and actuator are controlled by a microprocessor that can direct the duration of the force application and the repeated application of the cyclic mechanical force. The cyclic mechanical forces are applied a plurality of times until the teeth are realigned and malocclusion is treated.

The present invention has several benefits and advantages. One benefit of the invention is its use to substantially markedly shorten the duration of orthodontic treatment as compared to the current technology.

An advantage of the invention is that craniofacial bone restructuring can be accomplished more rapidly than has been possible using previously known techniques.

Another benefit of the invention is an apparatus that can realign maloccluded teeth.

Still further benefits and advantages will be apparent to the skilled worker from the disclosure that follows.

BRIEF DESCRIPTION OF THE DRAWINGS

In the drawings forming a portion of this disclosure.

DETAILED DESCRIPTION OF THE INVENTION

Figure 1:
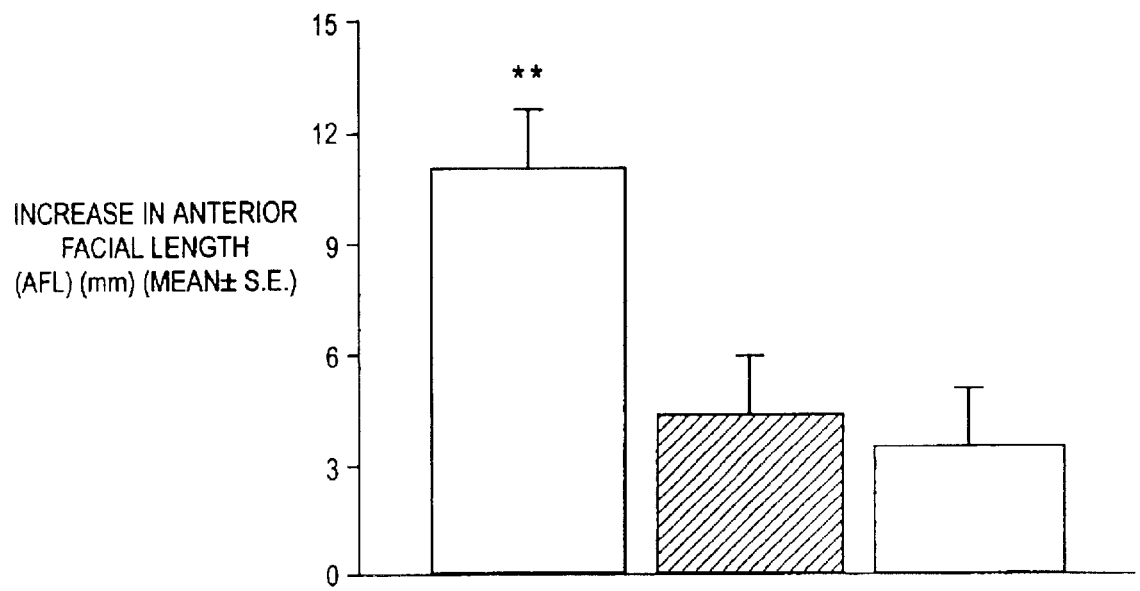
FIG. 1 shows bar graphs in which the increase in anterior facial length (AFL) of treated rabbits using a cyclic force application process of the present invention (left), a static force (center) or a sham control (right), and in which error bar tops are shown and double stars above the left graph indicate a statistically significant difference between those values and the values for each of the other two graphs. There is statistically greater amount of bone remodeling upon application of cyclic forces than both the sham control and static force.

Static forces have been used for more than a century to modulate osteogenesis of cranial sutures in not only laboratory research but also clinical practice. Cyclic forces are shown here to stimulate more effective sutural osteogenesis than static forces. Similarly, static forces have been orthodontically used for a much longer period of history the realignment of patients' teeth for treating malocclusion. Cyclic forces are similarly used here to achieve a desired orthodontic effect in a reduced period of time.

In accordance with the present invention, cyclic forces are used to expedite the remodeling of teeth and craniofacial bones in living mammal. Thus, this invention concerns the remodeling of a mammal's face by osteogenesis of the craniofacial bones or by realigning one or more of the mammal's teeth. Exemplary mammals are humans, apes, monkeys, rabbits, mice, rats and other laboratory animals as well as companion animals such as cats and dogs, and livestock such as pigs, goats, horses, cattle, sheep and the like.

More specifically, one aspect of the invention contemplates a method for inducing a predetermined amount of osteogenesis in the craniofacial bones of a mammal in need thereof. That method comprises the steps of (a) applying cyclical forces to a craniofacial suture of the mammal in which osteogenesis is desired with a peak magnitude of up to about 10 Newtons, and preferably about 0.1 to about 5 Newtons, and a frequency of up to about 40 Hz, and preferably about 0.1 to about 8 Hz for a predetermined period of time. That application is (b) repeated a plurality of times until a predetermined amount of osteogenesis is obtained.

Another aspect of the invention contemplates a method for realigning one or more of the teeth of a mammal in need thereof. That method comprises the steps of (a) applying cyclical forces to at least one tooth of the mammal in which tooth realignment is desired with a peak magnitude of up to about 10 Newtons, and preferably about 0.1 to about 5 Newtons, and a frequency of up to about 40 Hz, and preferably about 0.1 to about 2 Hz, in a direction of the desired realignment for a predetermined period of time. That application is (b) repeated a plurality of times until a predetermined amount of tooth realignment is obtained.

A cyclical force or force that is applied cyclically is a force that progresses from a first value to a second value and then back toward if not to the first value. That force can also return to a third value that is less than that of the first value and then return to or through the first value.

In an idealized situation, where the initial force is taken as zero at time zero, a cyclical force can resemble a sine wave over a given time period, which time period is referred to as the wave length. Thus, continuing with the idealized example, the first force value is zero, the second value is one, the force returns to zero and then to minus one and back to zero again before returning to one in the next cycle. There is no net force vector for each cycle of force application in this idealized example. This type of cyclical force is similar to a wiggle, and is particularly useful for inducing osteogenesis in craniofacial sutures.

In another type of cyclical force, there is a net directional vector to the force. Here, in a typical idealized situation, the first force at time zero can again be zero and the second force value can be one, but the third force value on average is greater than minus one so that there is an average net positive force vector for each cycle of force application. Preferably, the force value returns from the second value to about the first value in each cycle. Continuing the analogy from above to the sine wave, the type of force having a net vector can be analogized to a rectified or fully rectified wave that is formed on converting alternating current to direct current.

Continuing the wave form analogy further the peak magnitude of the force applied or the amplitude is up to about 10 Newtons (N), preferably up to about 5 N, and is more preferably up to about 2 Newtons. These amplitudes apply to either type of cyclical force. Minimal peak magnitude values are about 0.1 N.

The cycle time at which the application of force is repeated is the wavelength. The reciprocal of the wavelength measured in seconds is the frequency or cycles per second and is in units of Hertz (Hz). Illustrative cyclical forces are applied at about 0.1 to about 40 Hz, preferably at about 0.1 to about 8 Hz, more preferably at about 0.1 to about 2 Hz, more preferable still 0.2 to about 1.5 Hz, and most preferably at about 0.2 to about 1 Hz, although forces of higher frequency can further accelerate bone remodeling.

The cyclical force is applied for a predetermined time period. That time period is typically shorter where higher frequencies are used and longer where lower frequencies are used. A typical time period (duration for the application of the cyclic force) for the before-discussed frequencies is about one minute to about 30 minutes, and more preferably for about 5 minutes to about 20 minutes. Thus, the force is applied repeatedly. The time between repeated force applications can be minutes to days. Typically, the force is applied one or more times in each 24-hour time period (per day), and that application is repeated. When applied a plurality of times per day, the force is applied periodically such as every hour or every three hours, or the like.

These cyclical applications of force are continued until the desired or predetermined amount of osteogenesis or reduction of malocclusion (tooth realignment) is achieved. This time period is typically several months to up to about two years, depending on the degree of treatment required.

Although the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated.

Figure 2:
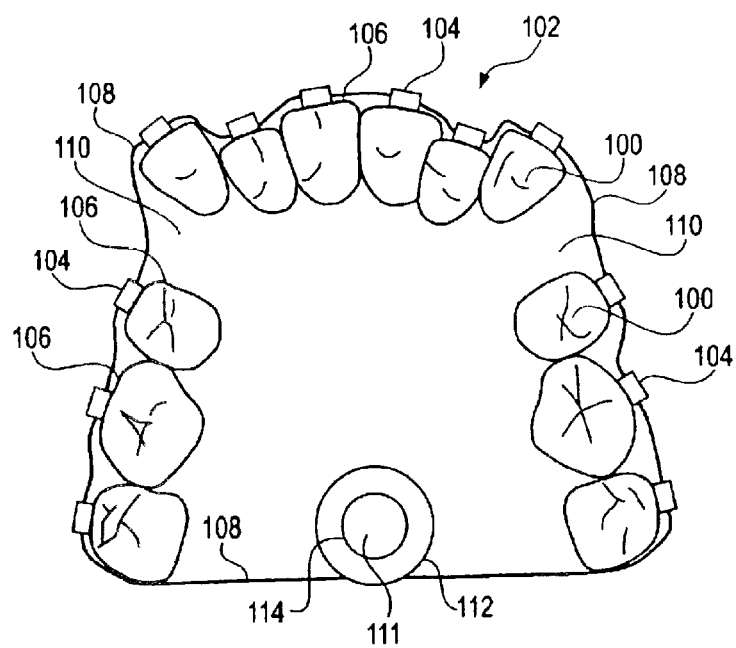
FIG. 2 is a diagrammatic view of an orthodontic device utilizing a device of the present invention in place in a human mouth having a malocclusion.

Referring now to FIG. 2, tooth 100, in a jaw having malocclusion, are shown having an intraoral orthodontic appliance 102 thereon. As is typical in such appliances, FIG. 2 shows that each tooth 100 has been fitted with a bracket 104, which is typically cemented to the outer surface 106 of each tooth, and a generally inelastic band 108, all made in a manner and of materials well known in the art. Band 108 is attached, through slots defined in each bracket 104 (as known in the art) to the brackets 104 and tightened. It is known that the band, of device of the prior art, generally is tightened at regularly scheduled orthodontist appointments throughout, typically, a six-month to two-year period. It will be seen, as the description proceeds, that the device of the present invention presents a means and method of continuously tightening a variation of such appliances throughout the treatment period.

As will be seen in FIG. 2, some of the teeth are separated by spaces 110, which may result from natural missing teeth, thumb or finger sucking or through dental extraction purposefully made to provide space for the movement of the teeth 100 to a pleasing position in the jaw. It will be understood by persons having skill in the art, that any of a plurality of orthodontic devices can be used, in manners well known in the art, in association with the device of the present invention, without departing from the novel scope of the present invention. It will also be understood that the present device can be used on fewer that all of the teeth in a jaw, such that corrective movement will be effected on only those teeth. The use of the devices illustrated herein is merely for illustrative purposes and is not meant as a limitation to the present invention.

Figure 4:
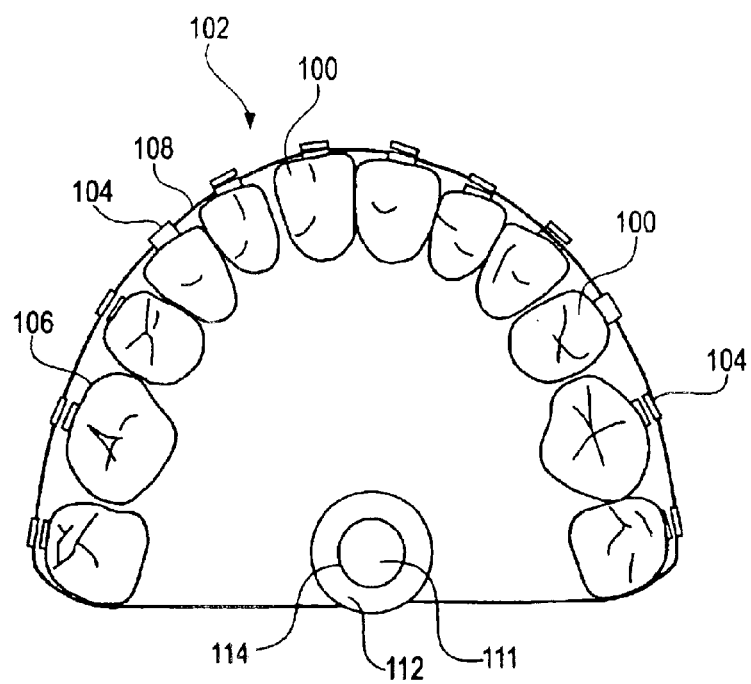
FIG. 4 is a diagrammatic view of the mouth and device of FIG. 2 after treatment with the device of the present invention.

As a departure from typical orthodontic devices of the prior art, and as shown in FIG. 2 and FIG. 4, the generally inelastic band 108 of the device of the present invention is formed as a continuous band, in that the ends of the band are joined at a centralized hub 111. As known to persons having skill in the art, typically, in prior art orthodontic devices the band is fixed to a tooth at each side of the jaw, and is therefore not continuous. It will also be known by persons having skill in the art that such devices are typically used simultaneously on the teeth of the upper and lower jaws. It will be understood by persons having skill in the art that the present invention can also be used simultaneously on the upper and lower jaws.

Figure 3:
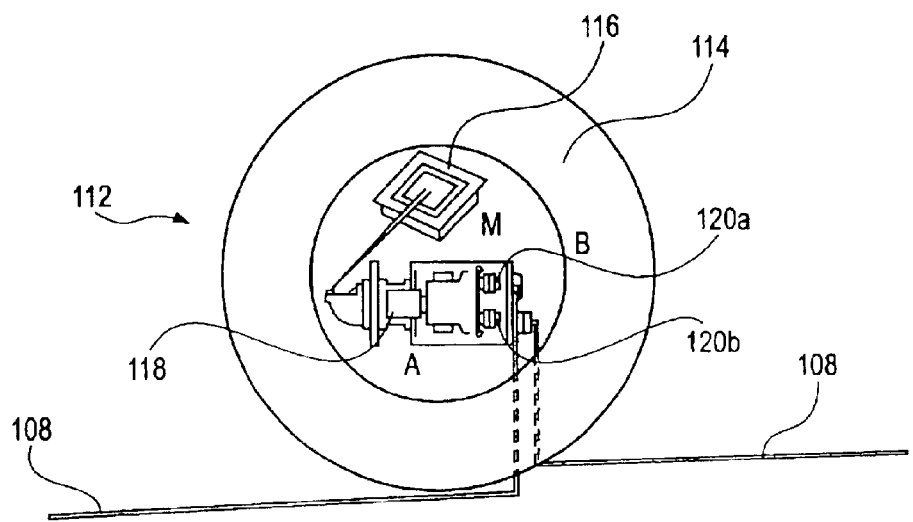
FIG. 3 is a diagrammatic representation of a device of the present invention.

FIGS. 5 and 7 further show a diagrammatic drawing of a cyclical-force assembly 112 located at the centralized hub 111 of the present invention. Referring now to FIG. 3, a more detailed diagrammatic view of the cyclical-force assembly 112 is shown. The outer container of the device 114 can be of any, sealed, moisture resistant type well known in the art, such that the items housed therein can be protected from the ambient conditions found in the mouth. Further, the housing can be of the type that provides means to maintain the items, housed therein, cool and at a necessary temperature range of operating conditions. Such housings, typically for any number of implantable electronic and chemical devices such as pacemaker, implantable defibrillators, insulin pumps and others, are well known in the art.

Within the outer container 114 of the cyclical-force assembly 112 of the present invention are housed a microprocessor 116, an actuator 118, two drive shafts 120a, 120b and a power source, typically a watch-battery type-cell (not shown). It is to be understood that a microprocessor and actuator of the type necessary for the operation of the present invention are well known in the art. Although these items, and watch battery-type cells, are shown and described, it is to be understood that any one or all of these items can be replaced with other elements without departing from the novel scope of the present invention. A motor and gears useful herein for a contemplated devise can be obtained from MicroMo Electronics, Inc., Clearwater Fla., USA.

In the operation of the cyclical-force assembly 112, microprocessor 116 is preprogrammed with a predetermined cycle and amplitude of forces to be applied by actuator 118 onto, cyclically, band 108 through drive shaft 120a and drive shaft 120b. As can be seen in FIG. 3, drive shafts 120a, 120b are attached, in a manner well known in the art, to the ends of band 108. It will be understood by persons having skill in the art that the connection of actuator 118 to band 108 can be made in any manner that allows the cyclical force of actuator drive shafts 120a and 120b to apply forces both in a pushing and pulling manner, as needed, to provide the necessary tension, and thus tooth realignment forces, to band 108. Such items as pulleys, rings, gears, angles and other devices can be used to permit the forces from actuator 118 to be effectively applied to band 108 without departing from the novel scope of the present invention.

The cyclical forces are applied to band 108 and thereby to the misaligned teeth causing, over a predetermined period, the correct alignment of the teeth, as shown in FIG. 4. It will be seen in FIG. 4, that, after a predetermined period of application of the cyclical forces of the present invention, the spaces 110 have been eliminated by the movement of the remaining teeth 100 into a more natural alignment. The desired alignment is further shown in the more graceful arc of band 108 about the outer surfaces 106 of the teeth 100.

The devise illustrated in FIGS. 2–4 is adapted for use intraorally and can be referred to as intelligent microprocesor-controlled braces (IMB). An extraoral devise can be similarly be prepared for reshaping cranial bones by inducing osteogenesis as cranial sutures.

ILLUSTRATIVE PROCEDURES

A total of twenty-four New Zealand White rabbits 6 weeks of age were used in these studies. Of those rabbits, 11 were used for acute studies and 13 were used for chronic studies.

The maxillae of different rabbits received exogenously supplied static forces with peak magnitude of 2 Newtons and a frequency of 0 Hz, as well as cyclic forces also at 2 Newtons but with frequencies of 0.2 and 1 Hz. The induced peak bone strain over the premaxillomaxillary suture did not differ significantly between the static forces (506 $\mu$strain.182; mean.S.D.), 0.2-Hz cyclic forces (436 $\mu$strain.191) and 1-Hz cyclic forces (461 $\mu$strain.229).

However, cyclic forces at 0.2 Hz delivered to the maxilla for 20 minutes per day over 12 days (240 cyclic per day) induced significantly more cranial growth ($p<0.01$), sutural separation and proliferation of osteoblast-like cells, in comparison with both sham controls and static forces of matching peak magnitude and duration. More significantly cyclic forces at 1 Hz delivered to the maxilla for 20 minutes per day over 12 days (1,200 cycles per day) induced more cranial growth ($p<0.01$), sutural separation and proliferation of osteoblast-like cells.

Thus, cyclic forces, although eliciting the same level of bone strain as static force of matching peak magnitude in craniofacial bones, induced significantly more osteogenesis and facial growth. These data demonstrate, for the first time, that extremely short dosages of cyclic forces induce more effective sutural osteogenesis than static forces, providing the basis for studying a wide range of cyclic forces with varying frequencies and daily dosages and their potential therapeutic use to modulate craniofacial osteogenesis.

Cyclic forces of 5 Newtons (N) and 0.2 Hz were applied to the maxillary incisors in the rabbit in vivo 20 minutes per day over 12 days (240 cycles per day). Static forces of matching peak magnitude and duration were applied in age- and sex-matched rabbits with additional rabbits as sham-operated controls.

On Day 1 and Day 13 of force delivery, standardized cephalometric X-ray films were taken, computer scanned and superimposed on preimplanted (immovable) markers to measure the overall and fractional facial lengths in the sagittal plane. Upon completion of force delivery, strain gages were implanted on the zygomatic arch to quantify bone strain in response to the cyclic forces, followed by harvesting the rabbit cranium: half for conventional histology and the other half for atomic force microscopy and computer-assisted histomorphometry.

The results of this study showed that the anterior facial length (AFL) of the rabbits loaded with cyclic forces (0.25 Hz and 5 N) in the sagittal plane was longer than the AFL in both sham-operated controls and those loaded with static forces of matching peak magnitude and duration. These quantifications were obtained by measuring the linear distance from the inion to the prosthion, which are defined as the most dorsal and ventral borders of the cranium in the sagittal plane respectively.

FIG. 1 illustrates that cyclic forces were more effective than static forces in causing bone growth and craniofacial remodeling. There was significantly more bone growth and therefore remodeling in the rabbit crania loaded with cyclic forces than static forces. The average anterior facial length (AFL) of the rabbits loaded with the cyclic forces was significantly longer ($p<0.01$) than the AFL in both sham-operated controls (right side bar) and those loaded with static forces (center bar) of matching peak magnitude and daily duration as revealed by Kruskal-Wallis test. No significant differences were found in the AFL between sham-operated controls and those loaded with static forces, suggesting that static forces were not effective in inducing craniofacial remodeling in the 12-day duration of the preliminary study.

The same trends were observed for the ratio of gain in the AFL over the gain of the posterior facial length; i.e., significant increase in the ratio of the AFL over the posterior facial length (p<0.01; Kruskal-Wallis test) and no significant differences between sham-operated controls and those loaded with static forces, indicating significantly more gain in the AFL than the gain in the posterior facial length in association with cyclic forces. The AFL was measured as the linear distance from the prosthion to the MOP (mesial to P1: first premolar), whereas the posterior facial length was measured as the linear distance from the MOP to the inion.

Histological evidence indicated wider separation of the premaxillomaxillary suture, frontonasal suture and maxillopalatine suture associated with cyclic loading. In contrast, sutures associated with control and static loads were less separated. New bone formation fronts were present in some of the sutures associated with cyclic loading upon high power examination. The sutural separation and osteogenesis appear to account for the greater gain in the anterior facial length shown in FIG. 1, above. The presence of marked sutural separation and craniofacial lengthening associated with in vivo cyclic forces at 5 Newtons, 0.2 Hz for 20 minutes per day over 12 days indicated the effectiveness of the treatment.

The zygomatic bone and squamosal bone across the zygomatiosquamosal suture were found to respond differently to anteriorly (ventrally) directed cyclic forces of 0.25 Hz and 5 Newtons peak-to-peak with two strain gages (ED-DY-062DW-350) (Measurements Group, Raleigh, N.C.) implanted above and below the zygomaticosquamosal suture in vivo. Whereas the squamosal bone experienced tensile strain, the zygomatic bone experienced compressive strain. In addition, the peak strain values are different: +100 microstrain (positive value denoted to tensile strain) for the squamosal bone and −300 microstrain (negative value denoted to compressive strain) for the zygomatic bone. These differential strain magnitude and contrasting strain patterns suggest probable activation of sutural osteoblasts via one of the several models of coupling between biomechanical stimuli and osteogenesis initiation such as fluid movement and direct coupling across the cell membrane, both of which appear more effectively accomplished by cyclic forces than static forces.

Additional in vivo bone strain recordings demonstrated that cyclic forces induced dynamic bone strain; i.e., both tensile and compressive, over the zygomaticosquamosal suture, whereas static forces of matching magnitude induced no dynamic change in bone strain. These recordings were obtained with a strain gage (ED-DY-062DW-350; Measurements Group) implanted "over" the zygomaticosquamosal suture with the longitudinal axis of the gage parallel to the course of the suture and with half of the gage on the squamosal bone and the other half on the zygomatic bone.

Although the peak cyclic and static bone strain was similar at approximately −140 to −150 microstrain, the effects of cyclic and static bone strains on the cortical bone surface are likely very different. Cyclic forces likely have induced dynamic strain in both the cortical bone surface and the suture with consequent activation of osteogenic cells for initiation of osteogenesis. This strain-induced osteogenesis, apparently never reported before in craniofacial bones, is consistent with a generally accepted view in long bones that cyclic strain per se or the fluid movement in bone induced by cyclic strain, instead of static strain, are the effective stimuli for osteogenesis.

Each of the patents, applications and articles cited herein is incorporated by reference. The use of the article "a" or "an" is intended to include one or more.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed is:

1. A method for realigning one or more of the teeth of a mammal in need thereof that comprises the steps of
   (a) applying cyclical forces to at least one tooth of the mammal in which tooth realignment is desired with a peak magnitude of about 0.1 to about 5 Newtons and a frequency of about 0.1 to about 2 Hz in a direction of the desired realignment for a predetermined period of time; and
   (b) repeating said application a plurality of times until a predetermined amount of tooth realignment is obtained.

2. The method according to claim 1 wherein said cyclical forces are repeatedly applied a plurality of times each day.

3. The method according to claim 2 wherein said cyclical forces are repeatedly applied over a period of days.

4. The method according to claim 1 wherein said peak magnitude is about 2 Newtons.

5. A method for realigning one or more of the teeth of a mammal in need thereof that comprises the steps of
   (a) applying cyclical forces to at least one tooth of the mammal in which tooth realignment is desired with a peak magnitude of up to about 10 Newtons and a frequency of about 0.1 to about 40 Hz in a direction of the desired realignment for a predetermined period of time;
   (b) repeating said application a plurality of times each day until a predetermined amount of tooth realignment is obtained.

6. The method according to claim 5 wherein said cyclical forces are repeatedly applied over a period of months.

7. The method according to claim 5 wherein said cyclical forces are applied at a frequency of about 0.1 to about 2 Hz.

* * * * *